(12) United States Patent
Miller (10) Patent No.: US 12,176,090 B2
(45) Date of Patent: *Dec. 24, 2024

(54) SYSTEMS AND METHODS FOR RECOMMENDING PHYSICAL ACTIVITY ASSOCIATED WITH MEDIA CONTENT

(71) Applicant: Adeia Guides, Inc., San Jose, CA (US)

(72) Inventor: Jeffrey P. Miller, Santa Clara, CA (US)

(73) Assignee: Adeia Guides Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/371,860

(22) Filed: Sep. 22, 2023

(65) Prior Publication Data

US 2024/0013890 A1 Jan. 11, 2024

Related U.S. Application Data

(63) Continuation of application No. 17/141,949, filed on Jan. 5, 2021, now Pat. No. 11,804,291.

(51) Int. Cl.
*G16H 20/30* (2018.01)
*G06V 20/40* (2022.01)
*H04N 21/25* (2011.01)

(52) U.S. Cl.
CPC ............ *G16H 20/30* (2018.01); *G06V 20/41* (2022.01); *H04N 21/251* (2013.01)

(58) Field of Classification Search
CPC ... G16H 20/30; G06K 9/00718; H04N 21/251
USPC ........................................................ 725/136
See application file for complete search history.

(56) References Cited

U.S. PATENT DOCUMENTS

| | | | |
|---|---|---|---|
| 10,489,016 B1 * | 11/2019 | Yue | H04N 21/4826 |
| 10,904,617 B1 | 1/2021 | Labarre et al. | |
| 11,804,291 B2 | 10/2023 | Miller | |
| 2001/0056477 A1 | 12/2001 | Mcternan et al. | |
| 2014/0026201 A1 | 1/2014 | Srinivasan et al. | |
| 2016/0163224 A1 * | 6/2016 | Rauhala | G09B 19/003 434/257 |
| 2016/0182955 A1 | 6/2016 | Klappert et al. | |
| 2018/0376178 A1 | 12/2018 | Cormican | |
| 2021/0252369 A1 | 8/2021 | Devine et al. | |
| 2021/0342952 A1 * | 11/2021 | Putnam | A63B 71/0622 |
| 2022/0215924 A1 | 7/2022 | Miller | |

* cited by examiner

*Primary Examiner* — Nnenna N Ekpo
(74) *Attorney, Agent, or Firm* — Haley Guiliano LLP (57) ABSTRACT

Systems and methods are presented herein for providing a user with a recommendation for physical activity related to media content. The user may activate a recommendation application setting on a user equipment device. The user may select a media asset for presentation on a user equipment device. The system may analyze data associated with the media asset and perform deep video analysis of the frames of the media asset to identify events in the media asset. The system may identify the content type of each respective segment of the media asset and may identify respective activities performed in each segment by a primary character. The system may determine a respective activity to recommend to the user for reach respective segment of the media asset. The application may then determine a segment is being displayed for a user and generate an overlay representing a physical activity for the user to perform.

20 Claims, 9 Drawing Sheets

SYSTEMS AND METHODS FOR RECOMMENDING PHYSICAL ACTIVITY ASSOCIATED WITH MEDIA CONTENT

CROSS-REFERENCE TO RELATED APPLICATION

This application is a continuation of U.S. patent application Ser. No. 17/141,949, filed Jan. 5, 2021, the disclosure of which is hereby incorporated by reference herein in its entirety.

BACKGROUND

The present disclosure is directed to systems and methods for providing a recommendation for physical activity, and more particularly, to systems and methods that generate a recommendation for physical activity for the user based on events in media content.

SUMMARY

When a user is consuming media content provided by a content platform, a user may want to engage in a physical activity. In some instances, a user may have to find a separate application to enable alerts or notifications to perform physical activities. This method is deficient in that content of these alerts or notifications will be limited to the content the user inputs into the alerts or reminders. Additionally, the alerts or notifications may not be synchronized with the media content the user is consuming, unless the user manually reviews the media content and customizes alerts or reminders to reflect the subject matter of the media content. This method may also cause a user to lose interest in the media content in favor of pursuing a physical activity, as the user may be distracted from the media content.

In another approach, a user may find an application that generates exercise recommendations based on available exercises and workout plans loaded into the application's memory. This method is also deficient in that the loaded content may not be associated with the subject matter of the media content and may cause a user to stop consuming the media content in order to engage in the physical activity recommended by the application. Additionally, the user is limited to exercises preloaded in the application and may not be able to customize recommendations to align with media content the user has an interest in. The user may also have to stop consuming media content and search exercise recommendations available through the application to create a customized set of exercise recommendations.

These deficiencies are solved by the systems and methods described herein, which in some embodiments provide a recommendation for physical activity for the user to perform based on a user's consumption of media content, which may include a media content item. In some embodiments, a system may have encoded on it a recommendation application. The recommendation application may be capable of generating media content for presentation on a user equipment system. While the media content is generated for presentation, events may be determined from data associated with the media content that correspond to activities performed by characters of interest in the media content. An activity for the user to perform is determined based on the determined events of the media content and may be related to the events in the media content. A recommendation for the user to perform the determined activity may be generated for presentation, proximate to the occurrence of the event in the generated media content. The recommendation may consist of a graphic animated overlay depicting the determined physical activity with a written description of the activity.

These techniques solve the problems of the other approaches described above. In particular, the disclosed systems and methods do not require a user to stop consuming media content to pursue physical activity. Additionally, this approach does not require a user to manually program notifications or alerts to start exercising, nor does this approach require a user to manually search for recommended exercises in a database to try to synchronize the recommended activities with events that are occurring in the media content.

In some embodiments, the recommendation application may generate for presentation the media content by generating the media content for display on a system that the recommendation application is loaded onto. In some embodiments, the recommendation application may generate for presentation the recommendation for physical activity by generating the recommendation for physical activity for display on a system that the recommendation application is loaded onto that is also displaying the media content.

In some embodiments the recommendation application may identify an event within media content by retrieving metadata associated with the media content. In some embodiments, the recommendation application may identify an event within media content by analyzing video frame data in the media content. In some embodiments, the recommendation application may determine if other media content items available through a content platform have similar events as the first media content item selected. The recommendation application may utilize metadata and other computer-readable information about each respective media content item available for consumption to determine primary characters and respective activities based on event data retrieved or extracted from each respective media content item. The recommendation application may then generate for later presentation a series of recommended exercises and overlays when the user selects each respective media content item for playback.

In some embodiments, the recommendation application recognizes a plurality of events in media content as a plurality of respective physical activities performed by a character in the media content. In some embodiments, the recommendation application may determine that multiple events that involve the same activity are in a same media content item. In some embodiments, the recommendation application may determine there are a maximum number of times a same event will generate a recommendation in a particular media content item.

In some embodiments, the recommendation application may retrieve a user profile associated with a request to generate media content items and a request to generate recommendations for physical activity. The recommendation application may review user preferences associated with the user profile and may generate recommendations for physical activity based on the user preferences associated with the user profile. In some embodiments, the recommendation application determines if the user profile enabled the media recommendation setting within the user profile in response to a user input to enable the embodiments of the recommendation application described herein.

In some embodiments, the recommendation application generates overlays that may have an option for the user to close out the overlay before the segment is over. Should a user close the overlay before the segment is over, the recommendation application may save that interaction as an indication that the recommended exercise does not suit the user's interest or capabilities and may remove that exercise from future recommendations.

In some embodiments, the recommendation application may identify other user interests and preferences based on the user's interaction with other content platforms and applications on the user equipment device. The recommendation application may utilize the collected preference data to generate new recommended activity overlays and proactively analyze other media assets of related content types in anticipation that the user may enable the application during the playback of other future media assets.

In some embodiments, the recommendation application may review a first event and a second event in a media content item to determine a time difference between the first event and the second event. The recommendation application may compare the time difference to a predetermined threshold to determine whether to generate for presentation a recommendation proximate to the occurrence of the second event.

In some embodiments, the recommendation may identify an event in a media content item and may generate a prompt for the user to interact with to determine if a subsequent recommendation for activity may be generated during the presentation of the identified event in the media content item.

BRIEF DESCRIPTIONS OF THE DRAWINGS

The above and other objects and advantages of the disclosure will be apparent upon consideration of the following detailed description, taken in conjunction with the accompanying drawings, in which.

DETAILED DESCRIPTION

Methods and systems are provided herein for providing a recommendation for physical activity that is related to media content, which in some embodiments is a media content item, being consumed by a user.

The methods and/or any instructions for performing any of the embodiments discussed herein may be encoded on computer-readable media. Computer-readable media includes any media capable of storing data. The computer-readable media may be transitory, including, but not limited to, propagating electrical or electromagnetic signals, or may be non-transitory including, but not limited to, volatile and non-volatile computer memory or storage devices such as a hard disk, floppy disk, USB drive, DVD, CD, media cards, register memory, processor caches, Random Access Memory (RAM), etc.

Figure 1:
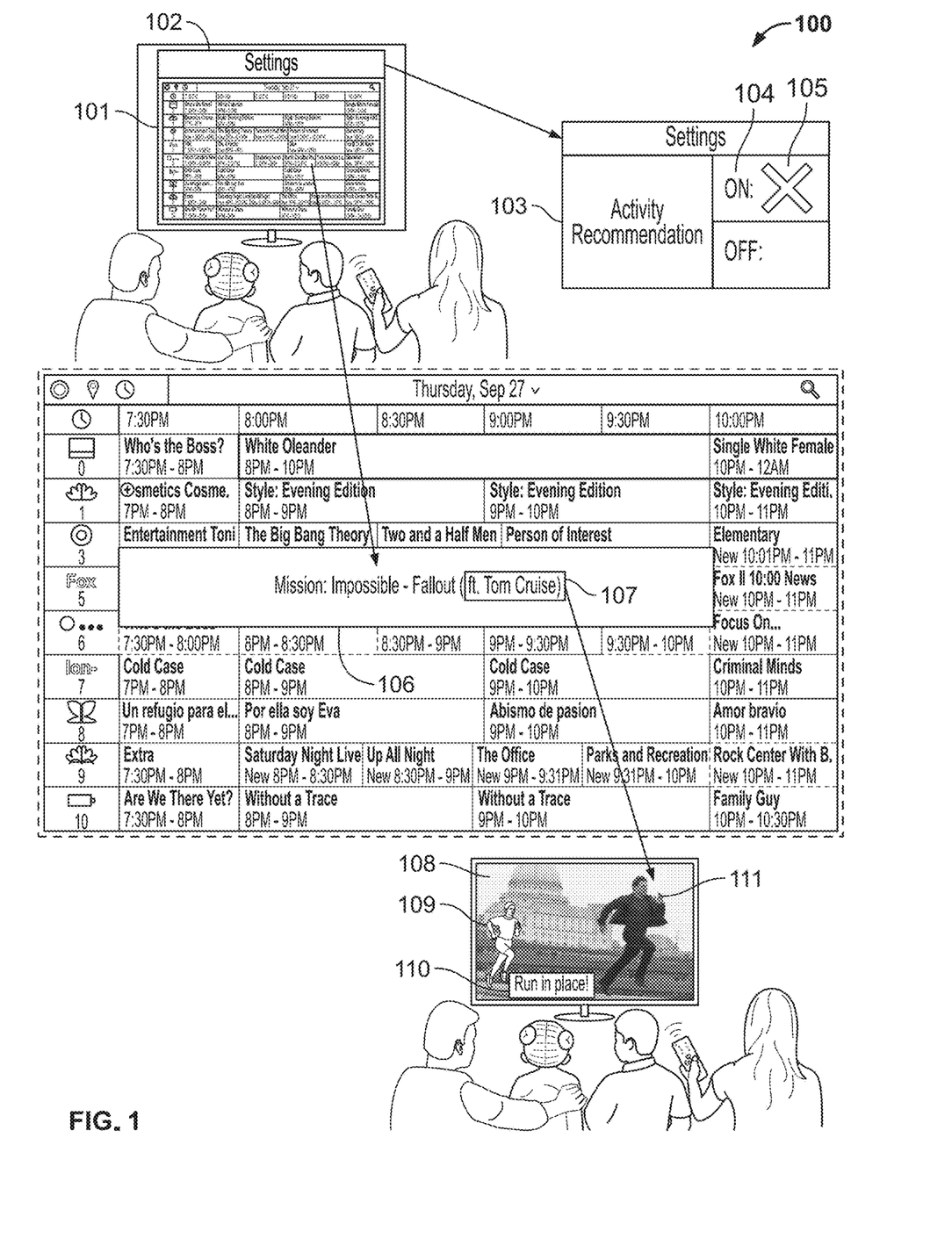
FIG. 1 depicts an illustrative audio/video user entertainment system, in accordance with some embodiments of the disclosure.

FIG. 1 depicts an illustrative audio/video user entertainment system 100, in accordance with some embodiments of the disclosure. The audio/video user entertainment system 100 may include audio outputs, video display 101, interactive menus, a microphone for recording a user's commands for the system, and a device such as a remote control, which receives user input (e.g., a text input in a field in an interactive interface to provide a command to the user entertainment system). In some embodiments, a user may want to enable the recommendation application. A user may interact with video display 101, which in some embodiments generates a selectable settings menu 102 that a user can interact with to adjust settings associated with the audio/video entertainment system 100. For example, selectable settings menu 102 may include activity recommendation setting 103 that includes an ON option 104 that a user can select. The application may recognize ON option 104 being selected by generating selected icon 105 that, when enabled, provides an indication to the recommendation application to analyze media assets to identify when to present activity recommendations.

Video display 101 may generate a list of media assets available for viewing for a user to select. In some embodiments, one or more of the media assets may be scheduled and available at a scheduled time. In some embodiments, one or more of the media assets may be available on a server for a user to select to start viewing without the constraint of a schedule. Each media asset may have a selectable icon 106, which, when selected, may inform the recommendation application that a particular media asset is selected for presentation. Each media asset may also have associated data 107, which in some embodiments enables the recommendation application to determine primary characters in the media asset whose activities will be tracked to generate physical activity recommendations. For example, a user may select a movie such as "Mission: Impossible—Fallout," which may include associated data that indicates the actor Tom Cruise portrays a primary character in the movie. The recommendation application may then identify Tom Cruise as subject 111 who may be tracked throughout the frames of the media asset for activities.

In some embodiments, the application analyzes the media asset by steps that may comprise identifying media asset segments (e.g., segment 108), analyzing the media asset frames per segment for elements, identifying subject 111 in each frame, and identifying the activity of subject 111. The application may then generate a recommended user activity by presenting graphic icon 109 and descriptive text 110. In some embodiments, the media asset segments are identified by reviewing of metadata associated with the media content to determine if a series of frames comprises a scene within the media asset. In some embodiments, the media asset segments are identified by performing deep video analysis of the media asset frames to determine if a series of frames can be considered part of a scene (e.g., based on the activities of primary characters), which may then be identified as a segment. In some embodiments, the subject 111 may be identified by the application reviewing the metadata associated with the media content to determine which segments subject 111 is visible in. In some embodiments, subject 111 may be identified by the application performing deep video analysis of each respective frame in a media asset to determine if a series of frames include subject 111. In some embodiments, the activity of subject 111 may be identified by the application reviewing the metadata associated with the media content to determine the activities subject 111 is performing in each respective frame or segment. In some embodiments, the activity of subject 111 may be identified by the application utilizing deep video analysis to analyze each frame for detectable activities being performed by subject 111.

In some embodiments, the recommended user activity may be determined by the application comparing data extracted from each media asset segment to a database of recommended physical activities available in storage (e.g., storage 316 of computing device 300 of FIG. 3) and then determining the recommendation based on a match between the data associated with a respective segment and a recommendation found in the database. In some embodiments, the generation of a recommended user activity comprises presenting graphic icon 109 and descriptive text 110 may be performed by the application utilizing deep video analysis data of the activity of subject 111 to generate graphic icon 109 in an outline of subject 111 and animated to perform a character activity related to with descriptive text 110, which may be generated by the application based on metadata related to the activity of subject 111 in the related frame or segment.

In some embodiments, a promotional overlay may also be generated which is related to graphic icon 109 and descriptive text 110. In some embodiments, the promotional overlay may be related to browsing activity related to a user profile associated with the user who has selected the media asset for presentation.

Figure 2:
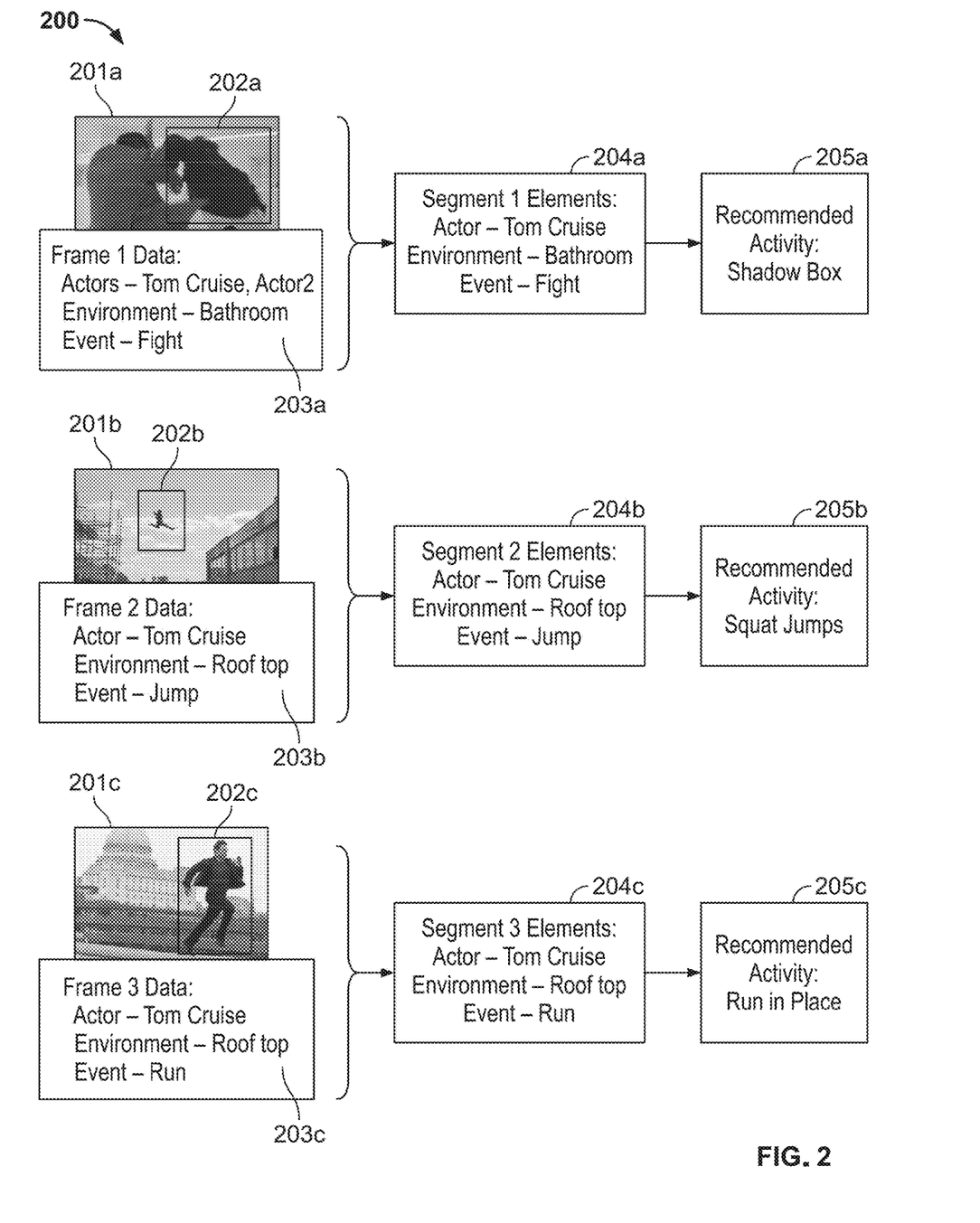
FIG. 2 depicts the recommendation application performing an illustrative analysis of frames of a media asset, in accordance with some embodiments of the disclosure.

FIG. 2 depicts the recommendation application performing an illustrative analysis 200 of frames of a media asset. In some embodiments, analysis 200 may start by identifying respective frames 201*a-d* of a media asset selected for presentation, e.g., "Mission: Impossible—Fallout" featuring Tom Cruise. In some embodiments, the application may be capable of performing deep video analysis that includes identifying respective characters and character activities 202*a-d* in each respective frame 201*a-d*. For example, the actor Tom Cruise may be seen fighting, jumping, running, and rock climbing in different scenes throughout the movie "Mission: Impossible—Fallout," and the application may identify these events based on deep video analysis seeking figures that resemble Tom Cruise in each respective frame. In some embodiments, the application may determine respective frame data 203*a-d* (e.g., data that identifies an Actor, an Environment, and an Event) for each respective frame 201*a-d* by utilizing metadata associated with the frames of the media asset. For example, metadata may identify actors, an environment, and an activity occurring in each frame or series of frames.

In some embodiments, the application may utilize metadata associated with frames 201*a-d* to identify respective segment element groups 204*a-d*, which may be used to define a segment within the media asset. In some embodiments, the application may generate a different activity recommendation (e.g., overlaid on the media content) for different segments of the movie. In some embodiments, the application may group a plurality of frames into a segment when the frames match each of the elements listed in one of respective segment element groups 204*a-d*. For example, a respective segment element group may include an actor name that may be Tom Cruise, an environment type that may be a rooftop, and an activity of the actor that may be running. In some embodiments, a frame may be analyzed by either a review of metadata or deep video analysis of the frame to determine the content of the frame. For example, a frame may have Tom Cruise running as identified in frame 201*c* and may have metadata represented by frame data 203*c*, which includes identifiers for the actor Tom Cruise in the environment of a rooftop and the event where the actor is running. In this example, the depicted frame may match the elements of segment element group 204*c*, and additional frames with like data may also be grouped in the same segment as frame 201*c*.

In some embodiments, the application may use the elements of respective segment element groups 204*a-d* to identify respective recommended activities 205*a-c*. In some embodiments, the application may utilize the activity identified in respective segment element groups 204*a-d*, e.g., running, as shown in segment element group 204*c*. In some embodiments, the application may utilize the activity identified in respective frame data 203*a-d* that is associated with the event, e.g., running, as shown in respective frame data 203*c*. In some embodiments, the application may utilize the results of deep video analysis of respective frames 202*a-d*, e.g., Tom Cruise running in respective frame 202*c*. The recommended activity generated in exemplary respective recommended activity 205*c* may be "Run in Place," which may correlate to the respective data source that was analyzed for generating the recommendation. The application may utilize any of the described analysis options alone or in combination, depending on the processing capabilities enabled on the system on which the recommendation application is implemented.

Figure 3:
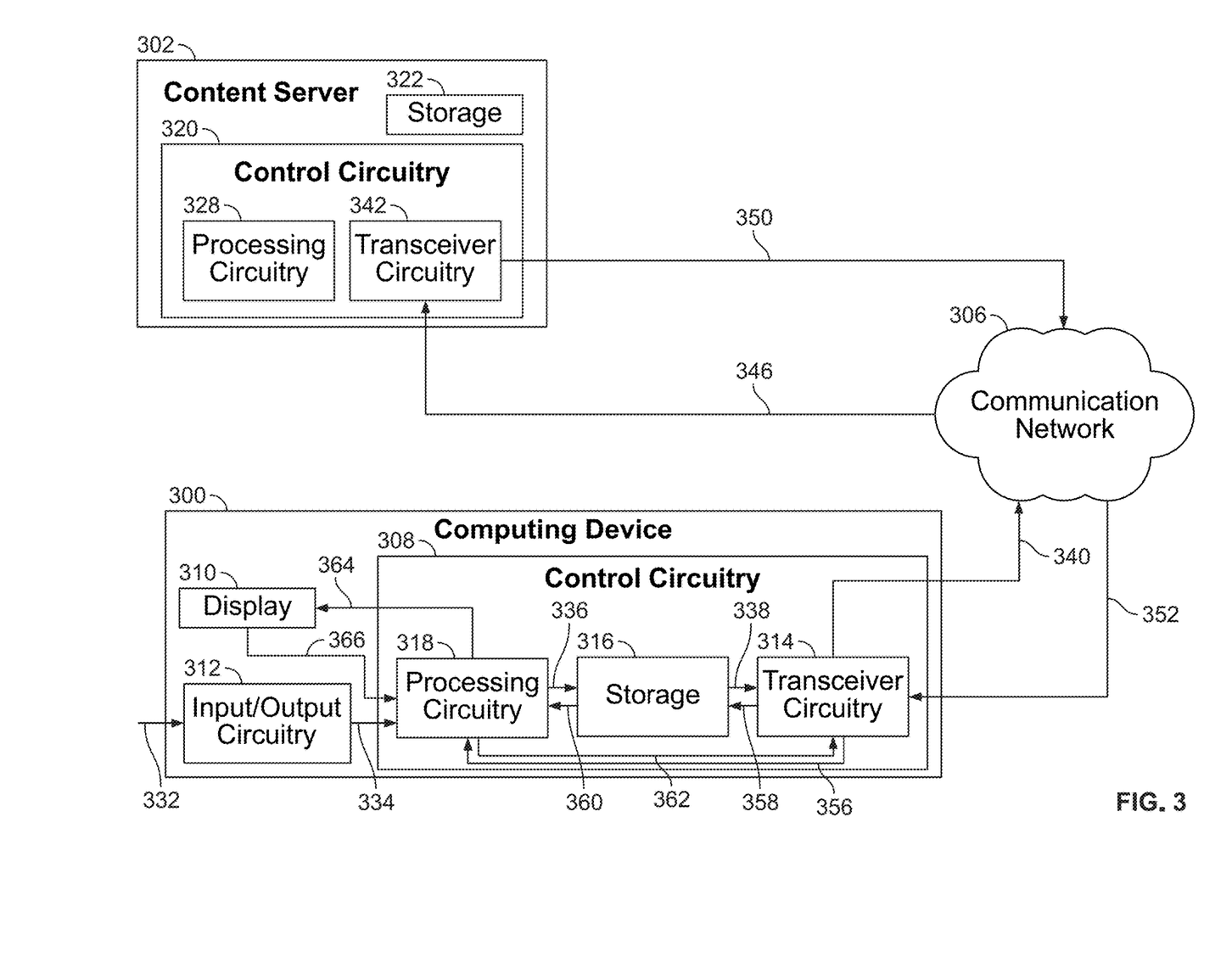
FIG. 3 is a block diagram representing devices, components of each device, and the transfer of data therebetween for an audio/video user entertainment system incorporating physical activity recommendation features, in accordance with some embodiments of the disclosure.

In some embodiments, the application is capable of accessing content server 302, e.g., as shown in FIG. 3. The application is capable of utilizing the processing of multiple modules connected by communication network 306 to find and review the information available on content server 302.

FIG. 3 is an illustrative block diagram showing an interactive audio/video system for providing a recommendation for physical activity for the user based on events in media content, in accordance with some embodiments of the disclosure. In some embodiments, one or more parts of or the entirety of the interactive system may be configured as a system implementing various features, processes, and components of FIGS. 1, 2, and 4-8. Although FIG. 3 shows a certain number of components, in various examples, the interactive system may include fewer than the illustrated number of components and/or multiples of one or more of the illustrated number of components.

The interactive system is shown to include computing device 300, content server 302, and a communication network 306. It is understood that while a single instance of a component may be shown and described relative to FIG. 3, additional instances of the component may be employed. For example, content server 302 may include, or may be incorporated in, more than one server. Similarly, communication network 306 may include, or may be incorporated in, more than one communication network. Content server 302 is shown communicatively coupled to computing device 300 through communication network 306. While not shown in FIG. 3, content server 302 may be directly communicatively coupled to computing device 300, for example, in a system absent or bypassing communication network 306.

Communication network 306 may comprise one or more network systems, such as, without limitation, Internet, LAN, WiFi or other network systems suitable for audio processing applications. In some embodiments, the system of FIG. 3 excludes content server 302, and functionality that would otherwise be implemented by content server 302 is instead implemented by other components of the system depicted by FIG. 3, such as one or more components of communication network 306. In still other embodiments, content server 302 may work in conjunction with one or more components of communication network 306 to implement certain functionality described herein in a distributed or cooperative manner. Similarly, in some embodiments, the system depicted by FIG. 3 excludes computing device 300, and functionality that would otherwise be implemented by computing device 300 is instead implemented by other components of the system depicted by FIG. 3, such as one or more components of communication network 306 or content server 302 or a combination of the same. In other embodiments, computing device 300 works in conjunction with one or more components of communication network 306 or content server 302 to implement certain functionality described herein in a distributed or cooperative manner.

Computing device 300 includes control circuitry 308, display circuitry 310 and input/output circuitry 312. Control circuitry 308 may be based on any suitable processing circuitry and comprises control circuits and memory circuits, which may be disposed on a single integrated circuit or may be discrete components. As referred to herein, processing circuitry should be understood to mean circuitry based on one or more microprocessors, microcontrollers, digital signal processors, programmable logic devices, field-programmable gate arrays (FPGAs), application-specific integrated circuits (ASICs), etc., and may include a multi-core processor (e.g., dual-core, quad-core, hexa-core, or any suitable number of cores). In some embodiments, processing circuitry may be distributed across multiple separate processors or processing units, for example, multiple of the same type of processing units (e.g., two Intel Core i7 processors) or multiple different processors (e.g., an Intel Core i5 processor and an Intel Core i7 processor). Some control circuits may be implemented in hardware, firmware, or software. Control circuitry 308 in turn includes transceiver circuitry 314, storage 316 and processing circuitry 318. In some embodiments, computing device 300 or control circuitry 308 may be configured as varying embodiments of audio/video user entertainment system 100 of FIG. 1.

In addition to control circuitry 308 and 320, computing device 300, content server 302, may each include storage (storage 316 and storage 322, respectively). Each of storages 316 and 322 may be an electronic storage device. As referred to herein, the phrase "electronic storage device" or "storage device" should be understood to mean any device for storing electronic data, computer software, or firmware, such as random-access memory, read-only memory, hard drives, optical drives, digital video disc (DVD) recorders, compact disc (CD) recorders, BLU-RAY disc (BD) recorders, BLU-RAY 3D disc recorders, digital video recorders (DVRs, sometimes called personal video recorders, or PVRs), solid state devices, quantum storage devices, gaming consoles, gaming media, or any other suitable fixed or removable storage devices, and/or any combination of the same. Each storage 316 and 322 may be used to store various types of content, metadata, and/or other types of data (e.g., they can be used to record audio questions asked by one or more participants connected to a conference). Non-volatile memory may also be used (e.g., to launch a boot-up routine and other instructions). Cloud-based storage may be used to supplement storages 316 and 322 or instead of storages 316 and 322. In some embodiments, the user profile activity history, user profile preferences, and accessible media content may be stored in one or more of storages 316 and 322.

In some embodiments, control circuitry 320 and/or 308 executes instructions for an application stored in memory (e.g., storage 322 and/or storage 316). Specifically, control circuitry 320 and/or 308 may be instructed by the application to perform the functions discussed herein. In some implementations, any action performed by control circuitry 320 and/or 308 may be based on instructions received from the application. For example, the application may be implemented as software or a set of executable instructions that may be stored in storage 322 and/or 316 and executed by control circuitry 320 and/or 308. In some embodiments, the application may be a client/server application where only a client application resides on computing device 300, and a server application resides on content server 302.

The application may be implemented using any suitable architecture. For example, it may be a stand-alone application wholly implemented on computing device 300. In such an approach, instructions for the application are stored locally (e.g., in storage 316), and data for use by the application is downloaded on a periodic basis (e.g., from an out-of-band feed, from an Internet resource, or using another suitable approach). Control circuitry 308 may retrieve instructions for the application from storage 316 and process the instructions to perform the functionality described herein. Based on the processed instructions, control circuitry 308 may determine to execute elements of the embodiments of this disclosure in response to input received from input/output circuitry 312 or from communication network 306. For example, in response to a user providing inputs to activate entertainment system 100, control circuitry 308 may perform the steps of any of the processes depicted in FIGS. 1, 2, and 4-8, or processes relative to various embodiments.

In client/server-based embodiments, control circuitry 308 may include communication circuitry suitable for communicating with an application server (e.g., content server 302) or other networks or servers. The instructions for carrying out the functionality described herein may be stored on the application server. Communication circuitry may include a cable modem, an Ethernet card, or a wireless modem for communication with other equipment, or any other suitable communication circuitry. Such communication may involve the Internet or any other suitable communication networks or paths (e.g., communication network 306). In another example of a client/server-based application, control circuitry 308 runs a web browser that interprets web pages provided by a remote server (e.g., content server 302). For example, the remote server may store the instructions for the application in a storage device. The remote server may process the stored instructions using circuitry (e.g., control circuitry 308) and/or generate displays. Computing device 300 may receive the displays generated by the remote server and may display the content of the displays locally via display circuitry 310. This way, the processing of the instructions is performed remotely (e.g., by content server 302) while the resulting displays, such as the display windows described elsewhere herein, are provided locally on computing device 300. Computing device 300 may receive inputs from the user via input/output circuitry 312 and transmit those inputs to the remote server for processing and generating the corresponding displays. Alternatively, computing device 300 may receive inputs from the user via input/output circuitry 312 and process and display the received inputs locally, by control circuitry 308 and display circuitry 310, respectively.

Content server 302 and computing device 300 may transmit and receive content and data such as media content via communication network 306. For example, content server 302 may be a media content provider, and computing device 300 may be a smart television configured to download or stream media content, such as a live news broadcast, from content server 302. Control circuitry 320, 308 may send and receive commands, requests, and other suitable data through communication network 306 using transceiver circuitry 342, 314, respectively. Control circuitry 320, 308 may communicate directly with each other using transceiver circuitry 342, 314, respectively, avoiding communication network 306.

It is understood that computing device 300 is not limited to the embodiments and methods shown and described herein. In nonlimiting examples, computing device 300 may be a television, a Smart TV, a set-top box, an integrated receiver decoder (TRD) for handling satellite television, a digital storage device, a digital media receiver (DMR), a digital media adapter (DMA), a streaming media device, a DVD player, a DVD recorder, a connected DVD, a local media server, a BLU-RAY player, a BLU-RAY recorder, a personal computer (PC), a laptop computer, a tablet computer, a WebTV box, a personal computer television (PC/TV), a PC media server, a PC media center, a handheld computer, a stationary telephone, a personal digital assistant (PDA), a mobile telephone, a portable video player, a portable music player, a portable gaming machine, a smartphone, or any other device, computing equipment, or wireless device, and/or combination of the same capable of suitably displaying and manipulating media content.

Control circuitry 320 and/or 308 may be based on any suitable processing circuitry such as processing circuitry 328 and/or 318, respectively. As referred to herein, processing circuitry should be understood to mean circuitry based on one or more microprocessors, microcontrollers, digital signal processors, programmable logic devices, field-programmable gate arrays (FPGAs), application-specific integrated circuits (ASICs), etc., and may include a multi-core processor (e.g., dual-core, quad-core, hexa-core, or any suitable number of cores). In some embodiments, processing circuitry may be distributed across multiple separate processors, for example, multiple of the same type of processors (e.g., two Intel Core i9 processors) or multiple different processors (e.g., an Intel Core i7 processor and an Intel Core i9 processor). In some embodiments, control circuitry 320 and/or control circuitry 308 are configured to implement a media content operation system, such as systems, or parts thereof, that perform various processes described and shown in connection with FIGS. 1, 2, and 4-8, and/or systems carrying out the features described and shown relative to FIGS. 1, 2, and 4-8.

Computing device 300 receives user input 332 at input/output circuitry 312. For example, computing device 300 may receive a user input such as a user swipe or user touch, as previously discussed. In some embodiments, computing device 300 is a media device (or player) configured as entertainment system 100, with the capability to access media content. It is understood that computing device 300 is not limited to the embodiments and methods shown and described herein. In nonlimiting examples, computing device 300 may be a television, a Smart TV, a set-top box, an integrated receiver decoder (TRD) for handling satellite television, a digital storage device, a digital media receiver (DMR), a digital media adapter (DMA), a streaming media device, a DVD player, a DVD recorder, a connected DVD, a local media server, a BLU-RAY player, a BLU-RAY recorder, a personal computer (PC), a laptop computer, a tablet computer, a WebTV box, a personal computer television (PC/TV), a PC media server, a PC media center, a handheld computer, a stationary telephone, a personal digital assistant (PDA), a mobile telephone, a portable video player, a portable music player, a portable gaming machine, a smartphone, or any other television equipment, computing equipment, or wireless device, and/or combination of the same.

User input 332 may be received from a user selection-capturing interface that is separate from device 300, such as a remote-control device, trackpad or any other suitable user movement sensitive or capture devices, or as part of device 302, such as a touchscreen of display circuitry 310. Transmission of user input 332 to computing device 300 may be accomplished using a wired connection, such as an audio cable, USB cable, ethernet cable or the like attached to a corresponding input port at a local device, or may be accomplished using a wireless connection, such as Bluetooth, WiFi, WiMAX, GSM, UTMS, CDMA, TDMA, 3G, 4G, 4G LTE, 5G, or any other suitable wireless transmission protocol. Input/output circuitry 312 may comprise a physical input port such as a 3.5 mm audio jack, RCA audio jack, USB port, ethernet port, or any other suitable connection for receiving audio over a wired connection, or may comprise a wireless receiver configured to receive data via Bluetooth, WiFi, WiMAX, GSM, UTMS, CDMA, TDMA, 3G, 4G, 4G LTE, 5G, or other wireless transmission protocols.

Processing circuitry 318 may receive user input 332 from input/output circuitry 312 using communication path 334. Processing circuitry 318 may convert or translate the received user input 332 which may be in the form of gestures or movement, to digital signals. In some embodiments, input/output circuitry 312 performs the translation to digital signals. In some embodiments, processing circuitry 318 (or processing circuitry 328, as the case may be) carries out disclosed processes and methods. For example, processing circuitry 318 or processing circuitry 328 may perform processes of FIGS. 1, 2, and 4-8, respectively.

Processing circuitry 318 may provide requests to storage 316 by communication path 336. Storage 316 may provide requested information to processing circuitry 318 by communication path 338. Storage 316 may transfer, by communication path 338, a request for information to transceiver circuitry 314, which may translate or encode the request for information to a format receivable by communication network 306 before transferring the request for information by communication path 340. Communication network 306 may forward the translated or encoded request for information to transceiver circuitry 342 by communication path 346.

At transceiver circuitry 342, the translated or encoded request for information, received through communication path 346, is translated or decoded for processing circuitry 328, which will provide a response to the request for information (e.g., additional activities associated with an event) based on information available through control circuitry 320 or storage 322, or a combination thereof. The response to the request for information is then provided back to communication network 306 by communication path 350 in an encoded or translated format such that communication network 306, which can forward the encoded or translated response back to transceiver circuitry 314 by communication path 352.

At transceiver circuitry 314, the encoded or translated response to the request for information may be provided directly back to processing circuitry 318 by communication path 356, or may be provided to storage 316, through communication path 358, which then provides the information to processing circuitry 318 by communication path 360. Processing circuitry 318 may also provide a request for information directly to transceiver circuitry 314 though communication path 362, enabling storage 316 to respond to an information request, provided through communication 336, by communication path 360 that storage 316 does not contain information pertaining to the request from processing circuitry 318.

Processing circuitry 318 may process the response to the request received through communication path 356 or 360 and may provide instructions to display circuitry 310 for a notification to be provided to the users through communication path 364. Display circuitry 310 may incorporate a timer for providing the notification or may rely on inputs through input/output circuitry 312 from the user, which are forwarded through processing circuitry 318 through communication path 364, to determine how long or in what format to provide the notification. When display circuitry 310 determines the display has been completed (e.g., media content has completed a playback time or a user has exited out of a recommendation), a notification may be provided to processing circuitry 310 through communication path 366.

The communication paths provided in FIG. 3 between computing device 300, content server 302, communication network 306, and all subcomponents depicted are exemplary and may be modified to reduce processing time or enhance processing capabilities for each step in the processes disclosed herein by one skilled in the art.

Figure 4:
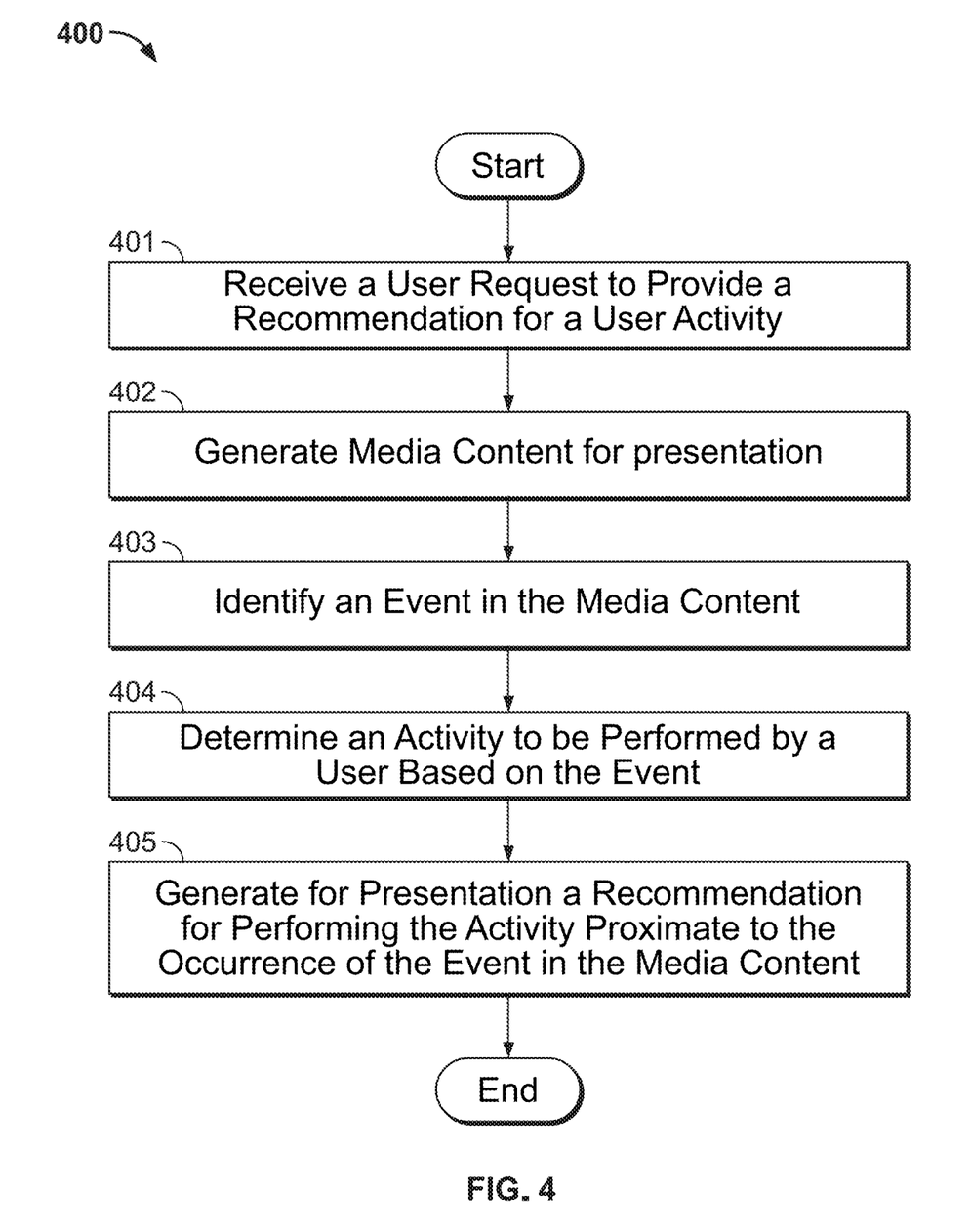
FIG. 4 is a flowchart of an illustrative process for generating a recommendation for physical activity that is related to media content being consumed by a user, in accordance with disclosed methods and embodiments.
Figure 5:
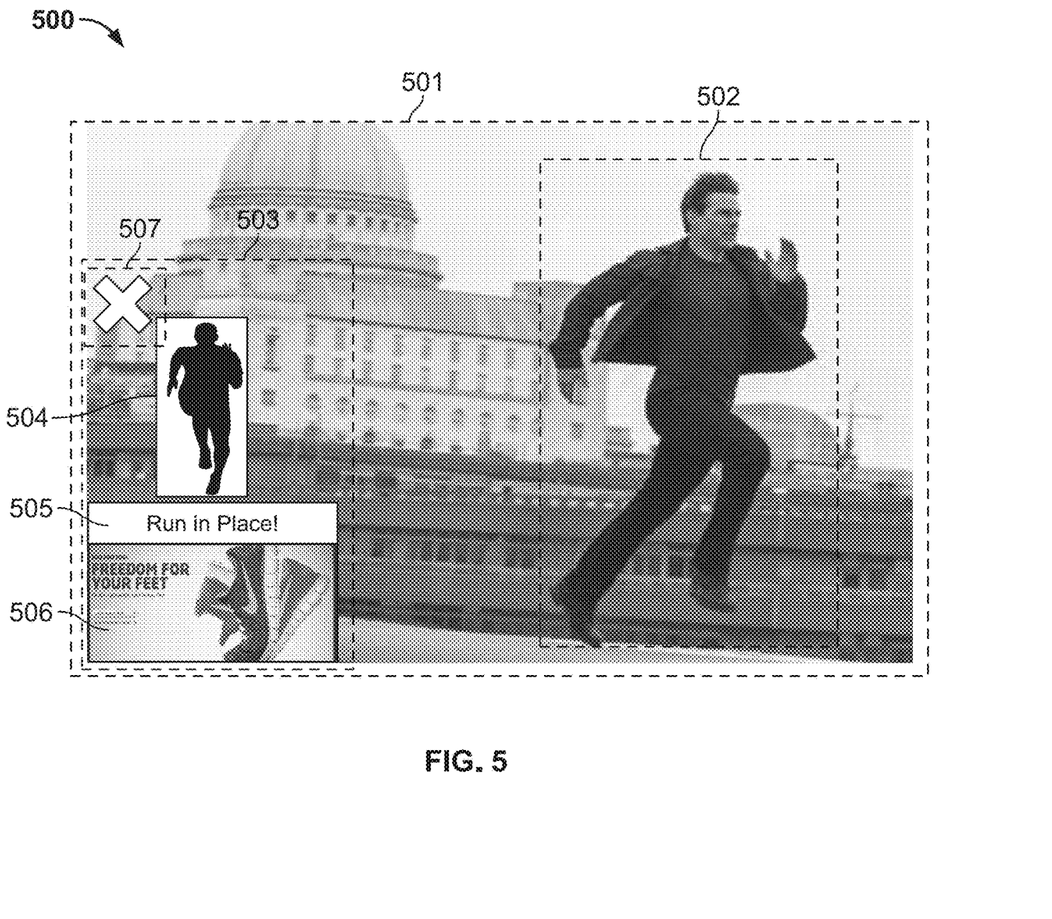
FIG. 5 illustrates an example of a generated overlay for a segment of a media asset that provides a recommendation for physical activity, in accordance with some embodiments of the disclosure.

FIG. 4 is a flowchart of illustrative process 400 for generating a recommendation for physical activity that is related to media content being consumed by a user, in accordance with some embodiments of the disclosure. Process 400 or any step thereof could be performed on, or provided by, any device shown in FIG. 3 and can incorporate various user interfaces (e.g., display 310 of FIG. 3). For example, process 400 may be executed by control circuitry 308 (FIG. 3) of computing device 300. In addition, one or more steps of process 400 may be incorporated into or combined with one or more steps of any other process or embodiment (e.g., process block 601 of process 600 depicted in FIG. 6, process block 701 of process 700 depicted in FIG. 7, or process block 801 of process 800 depicted in FIG. 8). FIGS. 1, 2, and 5 provide depictions of the execution of process 400.

At 401, the application may receive a user request to provide a recommendation for a user activity. In some embodiments, a user may interact with an interactive menu and select an icon to enable the application. In some embodiments, the user may speak a command to a user equipment device capable of receiving and processing audio user commands to enable the applications. In some embodiments, 401 is optional and the application may default to providing recommendations for user activity.

At 402, the application may generate media content for presentation to the user (e.g., using display 310 of FIG. 3). In some embodiments, the media content is generated for display to the user. In some embodiments, the media content is audibly generated for presentation to the user. In some embodiments, the media content is generated for presentation in response to a user selection of the media asset.

At 403, the application may identify an event in the media content. The event may, for example, be associated with a physical activity being presented in the media content as being enacted by a character in the media content. In some embodiments, the application identifies a primary character based on metadata associated with the media asset and tracks each frame for that primary character. In some embodiments, the application associates a primary character with a figure that is detected in a majority of the frames of the media asset through deep video analysis. The application may associate each respective segment to a content type, based on the primary activity detected in each segment of the media asset. In some embodiments, the media content includes predetermined metadata associated with particular events that, when detected, may notify the application of a recommended physical activity.

In some embodiments, there may be metadata associated with particular frames and corresponding segments that may indicate that the event does not last long enough during a particular segment of media content to generate a recommendation to a user. In some embodiments, the metadata associated with a particular event may not identify an activity that is associated with user preferences in a user profile and, as a result, the system may not flag that event for generating a recommendation. In some embodiments, a plurality of instances of the same activity may appear in the metadata of the media content for a plurality of segments. In some embodiments, the application may incorporate a threshold number of maximum instances of recommending a particular activity within media content and may limit the number of recommendations generated for a particular event type within a particular media content item.

At 404, the application determines an activity to recommend to the user based on the identified event. In some embodiments, determining a recommended activity may be accomplished by the application comparing data extracted from media asset segments to a preloaded database of recommended activities available in, for example, storage 316 of computing device 300 of FIG. 3. The recommendation activity may then be determined based on a match between the data associated with a respective segment and a recommendation found in the preloaded database. In some embodiments, determining a recommended activity may include the application utilizing deep video analysis data of the activity of the subject, e.g. subject 111 of FIG. 1 to generate an overlay icon that is an outline of the subject animated to perform the recommended activity. In some embodiments, determining an activity includes determining related promotional content that is related to the recommended activity and past user activity monitored on a user equipment device.

At 405, the application generates for presentation the recommendation for performing the activity associated with the segment by the analysis performed at 403 and at 404. In some embodiments, the recommendation includes an overlay that is comprised of a written description, a graphic display of an icon demonstrating the physical activity, and an area that incorporates promotional content. In some embodiments, the recommendation is a prompt that is generated, as a first overlay, for presentation prior to the event occurring in the media content, and the prompt may request a user input to determine if a second overlay with an animation incorporating the recommendation may be displayed for the user to interact with.

FIG. 5 illustrates an example of overlaid media content 500 for a segment of a media asset that provides a recommendation for physical activity, in accordance with some embodiments of the disclosure. The generated overlay may be provided by any device shown in FIG. 3 and can incorporate various user interfaces (e.g., display 310 of FIG. 3). For example, process 400 may be executed by control circuitry 308 (FIG. 3) of computing device 300 and may generate overlaid media content 500. In addition, one or more steps of process 400 may be incorporated into or combined with one or more steps of any other process or embodiment (e.g., process block 601 of process 600 depicted in FIG. 6) and may generate overlaid media content 500. FIGS. 1 and 2 provide depictions of the execution of process 400 with an example of overlay, in accordance with some embodiments of the disclosure.

Overlaid media content 500 may be generated by the application after the application performs a review of frame 501 of a media content item to determine the placement of sub-content area 503 within frame 501. In some embodiments, the application may utilize frame activity area 502 to determine where the viewer may have interest in frame 501 when a media asset is selected for presentation. In some embodiments, the application determines frame activity area 502 by deep video analysis, which may include identifying a character of interest, in accordance with some embodiments of the disclosure. In some embodiments, the application may utilize metadata, which may provide descriptions of what is displayed in each frame, to identify frame activity area 502. The application may define criteria for the amount of a frame that activity area 502 may cover, e.g., a threshold number of pixels, and may incorporate an exception that sub-content area 503 may overlap onto frame activity area 502 when frame activity area 502 encompasses a percentage frame area that is greater than a threshold.

Sub-content area 503 may be populated by animated recommendation 504, recommendation description 505, and promotional content 506. In some embodiments, sub-content area 503 may incorporate exit indicator 507 which, when selected, may close sub-content area 503 prior to the completion of the segment of the media asset sub-content area 503 was generated for. Animated recommendation 504 may be generated by retrieving information associated with analysis 200 in FIG. 2 which may be found in computing device 300 or content server 302 through communication network 306. In some embodiments, animated recommendation 504 may include a graphic animation representing the activity the user may perform for the duration of the related segment of the media asset. In some embodiments, animated recommendation 504 may be an icon that depicts the activity the user may perform for the duration of the related segment of the media asset. Recommendation description 505 may be generated by retrieving information associated with analysis 200 in FIG. 2, which may be found in computing device 300 or content server 302 through communication network 306. In some embodiments, recommendation description 505 may be a command associated with the activity demonstrated by animated recommendation 504. Promotional content 506 may be generated by retrieving information associated with analysis 200 in FIG. 2 that may be found in computing device 300 or content server 302 through communication network 306. In some embodiments, promotional content 506 may be associated with any or all of a user profile viewing history, user profile activity retrievable on computing device 300 or content server 302 through communication network 306, or any of the elements extracted during analysis 200 of FIG. 2.

Figure 6:
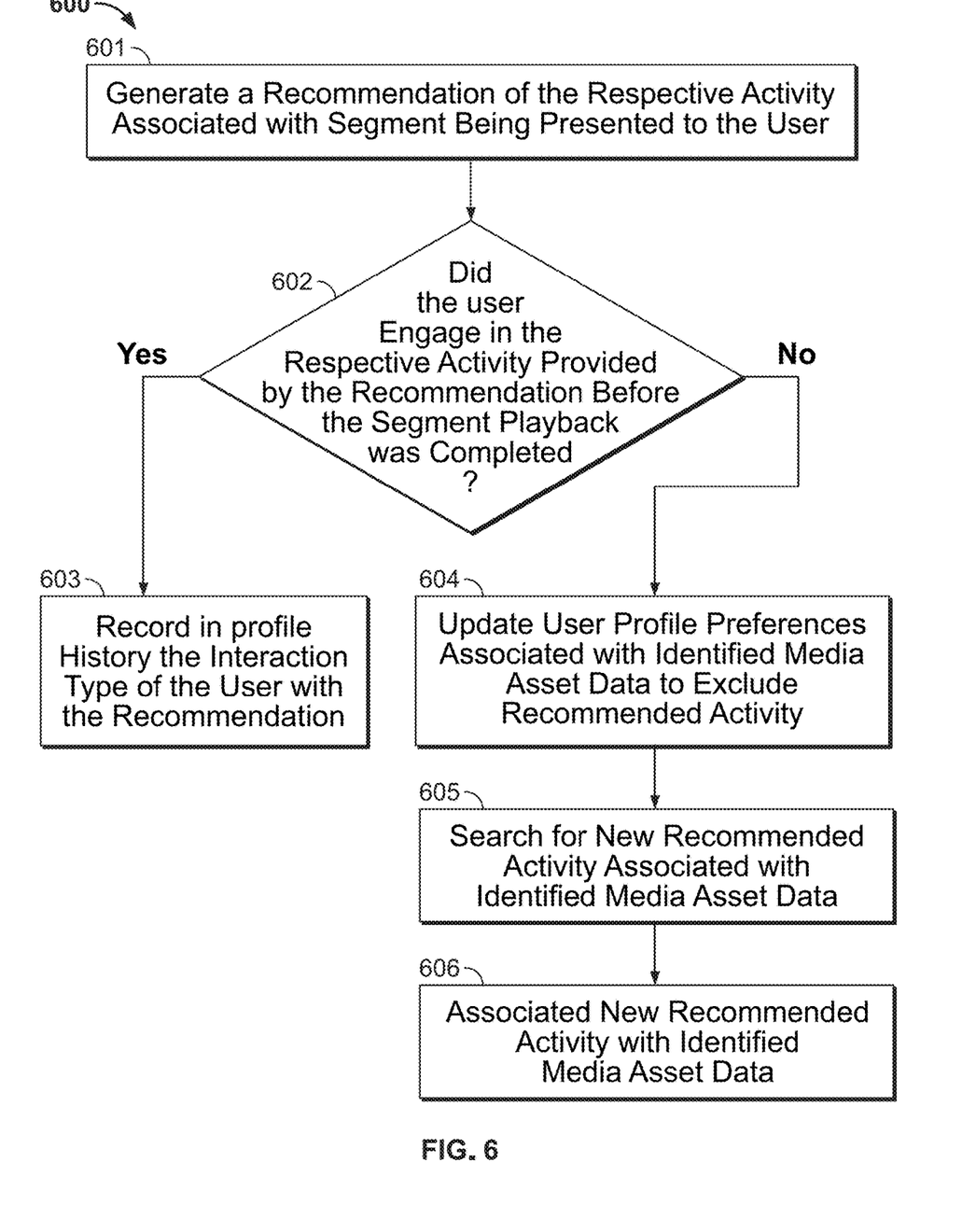
FIG. 6 is a flowchart of an illustrative process for updating user preferences based on a user's interaction with a generated recommendation for physical activity, in accordance with some embodiments of the disclosure.

FIG. 6 is a flowchart of illustrative process 600 for updating user preferences based on a user's interaction with a generated recommendation for physical activity, in accordance with some embodiments of the disclosure. Process 600 or any step thereof could be performed on, or provided by, any device shown in FIG. 3 and can incorporate various user interfaces (e.g., display 310 of FIG. 3). For example, process 600 may be executed by control circuitry 308 (FIG. 3) of computing device 300. In addition, one or more steps of process 600 may be incorporated into or combined with one or more steps of any other process or embodiment (e.g., process block 405 of process 400 depicted in FIG. 4, process block 701 of process 700 depicted in FIG. 7, or process block 801 of process 800 depicted in FIG. 8). FIGS. 1 and 2 provide depictions of the execution of process 600.

At 601, the application generates a recommendation of a respective activity associated with a segment of a media asset being presented to the user. In some embodiments, the overlay is generated using analysis 200 in FIG. 2. In some embodiments, the recommendation includes overlaid media content 500 shown in FIG. 5. For example, overlaid media content 500 incorporates multiple interactive elements such as promotional content 506 or exit indicator 507 or a combination of both. In some embodiments, the application may utilize motion sensors, cameras, or other forms of detection of user activity to determine if the user is engaging in the recommended activity. For example, input/output circuitry 312 of FIG. 3 may incorporate a plurality of user detection equipment to provide data to computing device 300 indicating that a user is engaged with the media content and the application. If the application determines that the user engaged in the recommended activity before the segment playback was completed (YES at 602), the application may proceed to record in the user profile history that the user accepted and enacted the recommended activity at 603. If the application determines that the user did not enact the activity in the recommendation (NO at 602), the application may update user profile preferences to exclude the recommended activity at 604.

At 605, the application may search a server for a new recommended activity associated with identified media asset data. In some embodiments, the application may determine the device used to play back the media asset is connected to content server 302 of FIG. 3 which may be connected to the user device by communication network 306, in accordance with some embodiments in the disclosure. At 606, the application may associate a new recommended activity to make part of overlaid media content 500, based on the results of the search at 605. In some embodiments, the application may update user profile preferences associated with the identified media asset data to include the new recommended activity associated at 606.

Figure 7:
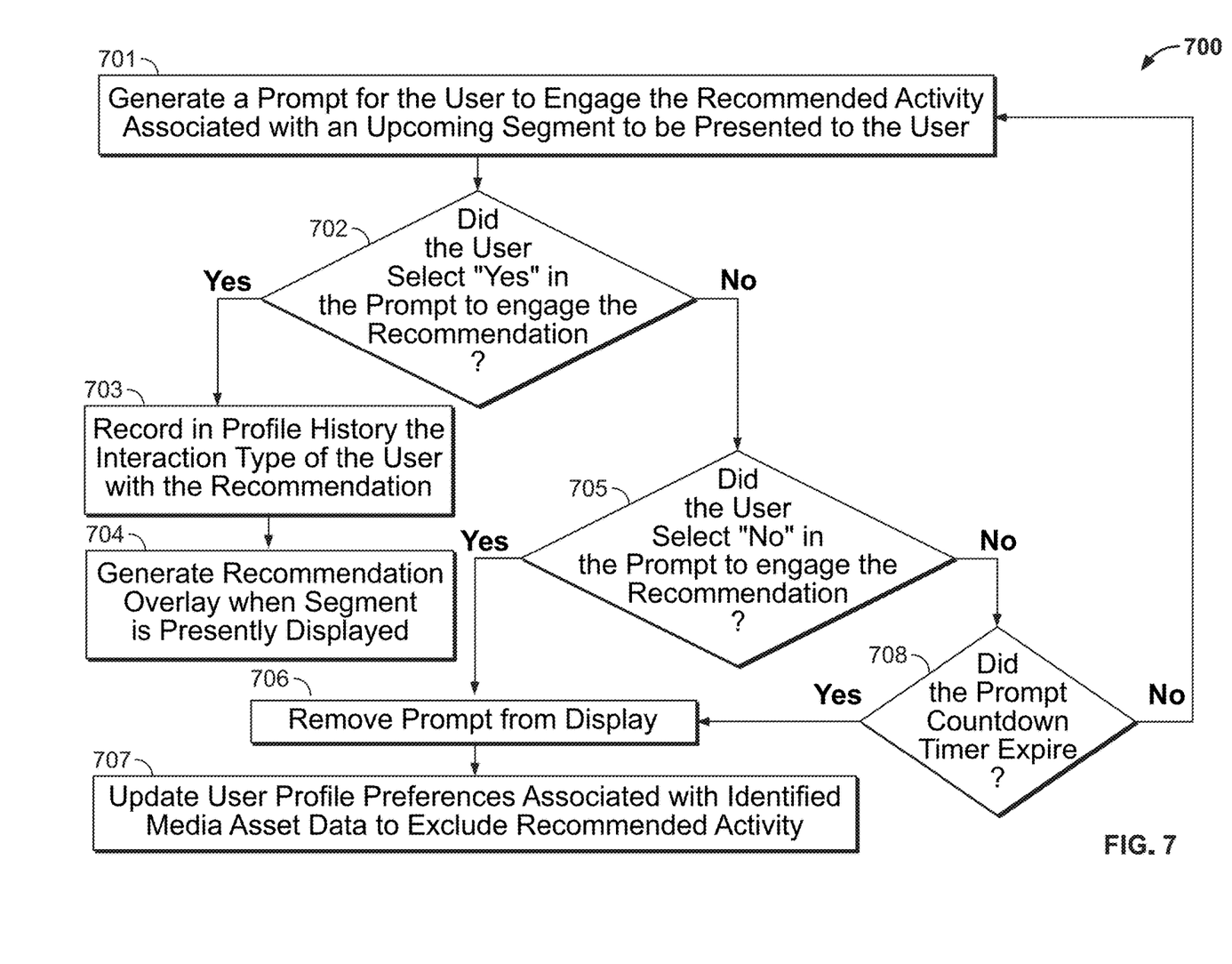
FIG. 7 is a flowchart of an illustrative process for updating user preferences based on a user's interaction with a generated prompt related to a recommendation for physical activity, in accordance with some embodiments of the disclosure.

FIG. 7 is a flowchart of an illustrative process for updating user preferences based on a user's interaction with a generated prompt related to a recommendation for physical activity, in accordance with some embodiments of the disclosure. Process 700 or any step thereof could be performed on, or provided by, any device shown in FIG. 3 and can incorporate various user interfaces (e.g., display 310 of FIG. 3). For example, process 700 may be executed by control circuitry 308 (FIG. 3) of computing device 300. In addition, one or more steps of process 700 may be incorporated into or combined with one or more steps of any other process or embodiment (e.g., process block 405 of process 400 depicted in FIG. 4, process block 601 of process 600 depicted in FIG. 6, or process block 801 of process 800 depicted in FIG. 8). FIGS. 1 and 2 provide depictions of the execution of process 700.

At 701, the application may generate a prompt for the user to engage a recommended activity associated with an upcoming segment of media content that may be presented to the user. In some embodiments, the application may utilize a predetermined period of time to determine when to generate the prompt prior to the event being generated for display to the user. In some embodiments, the application may determine that an upcoming segment incorporates an event that is associated with a recommended activity previously queued for the user. The application may, in response to determining a user recently engaged in the related activity, determine the upcoming segment will not be queued for generating a recommendation. In some embodiments, the application may generate the prompt utilizing the analysis to generate the overlay depicted in FIG. 5 to ensure the prompt does not obscure the media content that is generated for presentation to the user.

If the application determines that the user interacted with the prompt by indicating the user wants to engage the recommendation ("YES" at 702), the application may record in the activity history of the user profile that the user chose to engage the recommendation by viewing the overlay at 703. At 704, the application may generate the recommended overlay when the segment containing metadata associated with the event that occurs within that segment of the media content is generated for presentation for the user. In some embodiments, the application may rely on the analysis depicted in FIGS. 1, 2, and 4 to determine the content of the overlay to display. In some embodiments, the application generates the recommendation utilizing the overlay depicted in FIG. 5.

If the application determines that the user did not decide to interact with the prompt by indicating the user wants to engage the recommendation ("NO" at 702), the application may check at 705 if the user selected a "NO" indication in the prompt. If the application determines the user decided to not interact with the prompt by indicating the does not want to engage the recommendation ("YES" at 705), the application may remove the prompt from the generated display of the media content at 706. At 707, the application may update the user profile preferences associated with media asset data to exclude the recommended activity that was rejected by the user. If the application determines the user decided to not interact with the prompt by indicating the does not want to engage the recommendation ("NO" at 705), the application may check if the prompt countdown timer expired at 708. In some embodiments, the application has a predetermined amount of time that a prompt may be generated for display. The application may generate the prompt for display a predetermined amount of time before an event and the prompt may remain for display until a user interacts with the prompt or the timer expires. If the application determines the prompt countdown timer expired ("YES" at 708), the application may remove the prompt from the display at 706. If the application determines the prompt countdown timer did not expire ("NO" at 708), the application may continue generating the prompt until the application determines the user interacted with the prompt or the application determines the prompt countdown timer expired.

Figure 8:
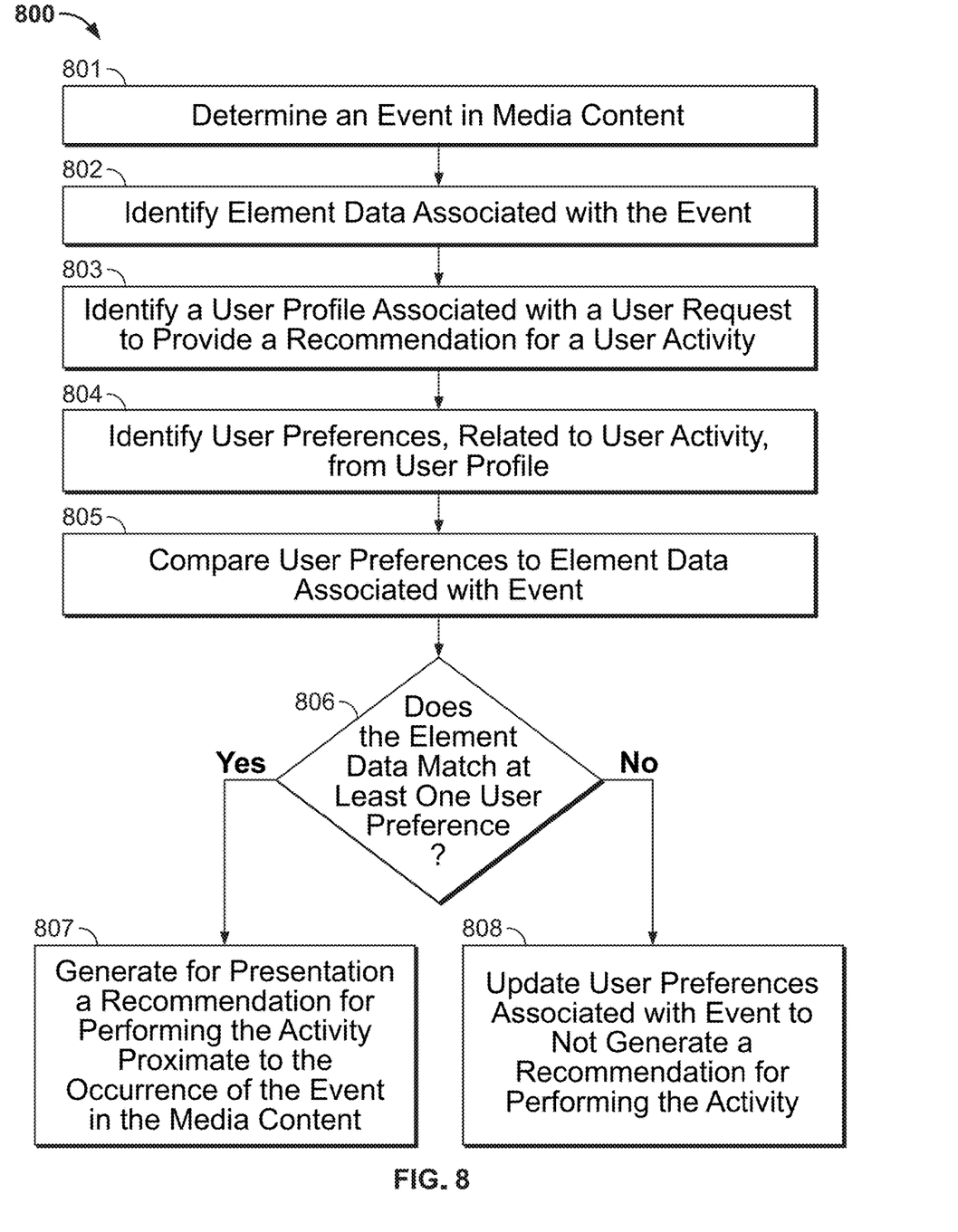
FIG. 8 is a flowchart of an illustrative process for utilizing user preferences to identify recommendations for physical activity, in accordance with some embodiments of the disclosure.

FIG. 8 is a flowchart of an illustrative process for utilizing user preferences to identify recommendations for physical activity, in accordance with some embodiments of the disclosure. Process 800 or any step thereof could be performed on, or provided by, any device shown in FIG. 3 and can incorporate various user interfaces (e.g., display 310 of FIG. 3). For example, process 800 may be executed by control circuitry 308 (FIG. 3) of computing device 300. In addition, one or more steps of process 800 may be incorporated into or combined with one or more steps of any other process or embodiment (e.g., process block 405 of process 400 depicted in FIG. 4, process block 601 of process 600 depicted in FIG. 6, or process block 701 of process 700 depicted in FIG. 7).

At 801, the application may determine an event is in a segment of media content. The application may utilize analysis 200 depicted in FIG. 2 or any other analysis one familiar with the art of the present disclosure may implement. At 802, the application may identify elements represented by data extracted utilizing a form of data analysis (e.g., analysis 200) that are associated with the event (e.g., actors in a frame, environment of the scene of the frame, event involving actors). At 803, the application may identify a user profile associated with a user request to provide a recommendation for a user activity and associated with media content to be generated for presentation. At 804, the application may identify user preferences related to user activities associated with the identified user profile. At 805, the application may compare the user preferences related to activities to the identified element data of an event identified in selected media content. If the application determines the element data matches at least one user preference ("YES" at 806), the application may generate for presentation a recommendation for performing the activity proximate to the occurrence of the event in the media content. For example, the recommendation can be presented a predetermined amount of time before the occurrence of the event and/or simultaneously with the occurrence of the event. If the application determines the element data does not match at least one user preference ("NO" at 806), the application may update the user preferences to not generate a recommendation for this media content and may update the user preferences to avoid generating a recommendation with future related events detected by the application in future media content selected for generation by the user profile.

The systems and processes discussed above are intended to be illustrative and not limiting. One skilled in the art would appreciate that the actions of the processes discussed herein may be omitted, modified, combined, and/or rearranged, and any additional actions may be performed without departing from the scope of the invention. More generally, the above disclosure is meant to be exemplary and not limiting. Only the claims that follow are meant to set bounds as to what the present disclosure includes. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real time. It should also be noted that the systems and/or methods described above may be applied to, or used in accordance with, other systems and/or methods.

While some portions of this disclosure may refer to "convention" or examples, any such reference is merely to provide context to the instant disclosure and does not form any admission as to what constitutes the state of the art.

What is claimed is:

1. A method for providing activity recommendations, comprising:
   generating for presentation to a user, via a content server, a media content item;
   determining an event occurring in the media content item, wherein the event comprises a physical activity comprising one or more actions performed by a character in the media content item;
   identifying element data associated with the event;

identifying, based on a user profile associated with the user, a plurality of user activity preferences;

determining whether the element data matches at least one user activity preference of the plurality of user activity preferences;

in response to determining that the element data matches at least one user activity preference, generating for presentation a recommendation for performing a corresponding user activity proximate to the occurrence of the event in the media content item; and in response to determining that the element data does not match at least one user activity preference, updating the user activity preferences with the event to refrain from generating a recommendation for performing the corresponding user activity.

2. The method of claim 1, wherein the element data comprises actor information, an environment type and an activity being performed by the actor.

3. The method of claim 1, wherein the user activity preferences are based on the user's interactions with a generated prompt related to a recommendation for corresponding user activity.

4. The method of claim 1, wherein the recommended corresponding user activity is different from the physical activity performed by the character in the media content item.

5. The method of claim 1, wherein determining the event occurring in the media content item comprises retrieving metadata associated with the media content item.

6. The method of claim 1, wherein determining the event occurring in the media content item comprises analyzing video frame data associated with the media content item.

7. The method of claim 1, wherein the user profile comprises a media recommendation setting and wherein the media recommendation setting is set in response to receiving a user input.

8. The method of claim 1, wherein the event comprises a first event, the method further comprising:
    identifying a second subsequent event in the media content item;
    determining a time difference between the first event and the second subsequent event;
    comparing the time difference to a predetermined threshold; and
    in response to comparing the time difference to the predetermined threshold, determining whether to generate for presentation a recommendation for performing a different corresponding user activity proximate to the occurrence of the second subsequent event.

9. The method of claim 1, wherein:
    the event in the media content item comprises an event type; and
    determining the corresponding user activity to be performed comprises:
        comparing the event type to event types of a plurality of user activities to be performed; and
        identifying a match based on the comparing.

10. The method of claim 1, wherein the generating for presentation to the user the media content item comprises generating the media content item for display on a display.

11. A system for providing activity recommendations, the system comprising:
    a memory; and
    a control circuitry configured to:
        generate for presentation to a user, via a content server, a media content item;
        determine an event occurring in the media content item, wherein the event comprises a physical activity comprising one or more actions performed by a character in the media content item;
        identify element data associated with the event;
        identify, based on a user profile associated with the user, a plurality of user activity preferences stored in the memory;
        determine whether the element data matches at least one user activity preference of the plurality of user activity preferences stored in the memory;
        in response to determining that the element data matches at least one user activity preference, generate for presentation a recommendation for performing a corresponding user activity proximate to the occurrence of the event in the media content item; and
        in response to determining that the element data does not match at least one user activity preference, update the user activity preferences with the event to refrain from generating a recommendation for performing the corresponding user activity.

12. The system of claim 11, wherein the element data comprises actor information, an environment type and an activity being performed by the actor.

13. The system of claim 11, wherein the user activity preferences are based on the user's interactions with a generated prompt related to a recommendation for corresponding user activity.

14. The system of claim 11, wherein the recommended corresponding user activity is different from the physical activity performed by the character in the media content item.

15. The system of claim 11, wherein the control circuitry is configured to determine the event occurring in the media content item by retrieving metadata associated with the media content item.

16. The system of claim 11, wherein the control circuitry is configured to determine the event occurring in the media content item by analyzing video frame data associated with the media content item.

17. The system of claim 11, wherein the user profile comprises a media recommendation setting and wherein the media recommendation setting is set in response to receiving a user input.

18. The system of claim 11, wherein the event comprises a first event, the control circuitry further configured to:
    identify a second subsequent event in the media content item;
    determine a time difference between the first event and the second subsequent event;
    compare the time difference to a predetermined threshold; and
    in response to comparing the time difference to the predetermined threshold, determine whether to generate for presentation a recommendation for performing a different corresponding user activity proximate to the occurrence of the second subsequent event.

19. The system of claim 11, wherein:
    the event in the media content item comprises an event type; and
    the control circuitry configured to determine the corresponding user activity to be performed by:
        comparing the event type to event types of a plurality of user activities to be performed; and
        identifying a match based on the comparing.

20. The system of claim 11, wherein the control circuitry is configured to generate for presentation to the user the media content item by generating the media content item for display on a display.

* * * * *